(12) United States Patent
Matsumoto et al.

(10) Patent No.: US 9,015,868 B2
(45) Date of Patent: Apr. 28, 2015

(54) FOG-RESISTANT STRUCTURE AND PROTECTIVE DEVICE FOR EYES

(75) Inventors: Kimio Matsumoto, Osaka (JP); Jindai Yamaguchi, Osaka (JP); Keishi Yoshikawa, Osaka (JP)

(73) Assignee: Yamamoto Kogaku Co., Ltd., Osaka (JP)

( * ) Notice: Subject to any disclaimer, the term of this patent is extended or adjusted under 35 U.S.C. 154(b) by 293 days.

(21) Appl. No.: 12/954,013

(22) Filed: Nov. 24, 2010

(65) Prior Publication Data

US 2011/0126345 A1    Jun. 2, 2011

(30) Foreign Application Priority Data

Dec. 2, 2009 (JP) ................................ 2009-274968

(51) Int. Cl.
*A61F 9/04* (2006.01)
*G02C 11/08* (2006.01)
*A61F 9/02* (2006.01)

(52) U.S. Cl.
CPC ................ *G02C 11/08* (2013.01); *A61F 9/028* (2013.01)

(58) Field of Classification Search
CPC ........... A61F 9/02; A61F 9/029; A61F 9/028; A41D 13/1176; A41D 13/1184; G02C 11/08
USPC .......... 2/6.3, 6.4, 6.5, 6.7, 425, 424, 15, 426, 2/427, 428, 429, 430, 431, 432, 434, 435, 2/442; 219/211
See application file for complete search history.

(56) References Cited

U.S. PATENT DOCUMENTS

| | | | | | |
|---|---|---|---|---|---|
| 2,569,773 | A | * | 10/1951 | Orr | 219/543 |
| RE25,711 | E | * | 1/1965 | Gaiser | 156/101 |
| 4,119,425 | A | * | 10/1978 | Marriott | 65/107 |
| 4,209,234 | A | * | 6/1980 | McCooeye | 351/62 |
| 4,543,466 | A | * | 9/1985 | Ramus | 219/203 |
| 4,584,721 | A | | 4/1986 | Yamamoto | |
| 4,638,728 | A | * | 1/1987 | Elenewski | 219/211 |
| 4,668,270 | A | * | 5/1987 | Ramus | 65/106 |

(Continued)

FOREIGN PATENT DOCUMENTS

| | | |
|---|---|---|
| DE | 2718679 A1 | 11/1978 |
| DE | 200 05 071 U1 | 6/2000 |

(Continued)

OTHER PUBLICATIONS

European Search Report for corresponding EP Application No. 10192830.7-2217, dated Apr. 11, 2011.

(Continued)

*Primary Examiner* — Alissa L Hoey
(74) *Attorney, Agent, or Firm* — Heslin Rothenberg Farley & Mesiti P.C.

(57) ABSTRACT

A fog-resistant structure and a protective device for eyes is configured such that a transparent conductive film is formed on one surface of a lens or shield, a linear electrode is provided on upper and lower portions of the surface of the lens or shield so that each of a central region and opposite side regions of the lens or shield has substantially equal spacing between the upper and lower linear electrodes. Thus each region of the lens or shield has no difference in temperature without regulating power supplied to the transparent conductive film, thereby eliminating wasted power consumption and allowing even a structure using a battery as the power supply to have much longer available time.

21 Claims, 10 Drawing Sheets

(56) References Cited

U.S. PATENT DOCUMENTS

| | | | | |
|---|---|---|---|---|
| 4,682,007 A | * | 7/1987 | Hollander | 219/211 |
| 4,847,472 A | * | 7/1989 | Koontz | 219/543 |
| 4,868,929 A | * | 9/1989 | Curcio | 2/435 |
| 4,942,629 A | * | 7/1990 | Stadlmann | 2/435 |
| 5,099,104 A | * | 3/1992 | Holzer et al. | 219/203 |
| 5,319,397 A | * | 6/1994 | Ryden | 351/62 |
| 5,351,339 A | * | 10/1994 | Reuber et al. | 2/9 |
| 5,354,966 A | * | 10/1994 | Sperbeck | 219/203 |
| 5,471,036 A | * | 11/1995 | Sperbeck | 219/522 |
| 5,500,953 A | * | 3/1996 | Reuber et al. | 2/9 |
| 5,671,483 A | * | 9/1997 | Reuber | 2/424 |
| 5,694,650 A | | 12/1997 | Hong | |
| 5,798,499 A | * | 8/1998 | Shibata et al. | 219/203 |
| 5,806,102 A | * | 9/1998 | Park | 2/424 |
| 5,845,342 A | * | 12/1998 | Park | 2/424 |
| 6,211,491 B1 | * | 4/2001 | Mazaki | 219/203 |
| 6,417,491 B1 | * | 7/2002 | Taniuchi | 219/211 |
| 6,701,537 B1 | * | 3/2004 | Stamp | 2/424 |
| 6,765,177 B2 | * | 7/2004 | Noguchi et al. | 219/203 |
| 7,648,234 B2 | * | 1/2010 | Welchel et al. | 351/62 |
| 8,136,170 B2 | * | 3/2012 | DiPaola | 2/435 |
| 2005/0045613 A1 | * | 3/2005 | Maeuser et al. | 219/203 |
| 2006/0290250 A1 | * | 12/2006 | Kuo | 313/23 |
| 2007/0221646 A1 | | 9/2007 | Shin et al. | |
| 2008/0290081 A1 | * | 11/2008 | Biddell | 219/203 |
| 2009/0025125 A1 | * | 1/2009 | Jou | 2/428 |
| 2009/0235438 A1 | * | 9/2009 | DiPaola | 2/435 |

FOREIGN PATENT DOCUMENTS

| | | |
|---|---|---|
| EP | 0 263 582 A1 | 4/1988 |
| EP | 0876082 A2 | 11/1998 |
| JP | 50-147192 A | 11/1975 |
| JP | 2002-237371 A | 8/2002 |
| WO | 2009 142447 A1 | 11/2009 |

OTHER PUBLICATIONS

European Patent Office Communication Pursuant to Article 94(3) EPC dated Jul. 11, 2012.

Office Action dated Feb. 27, 2013 issued in corresponding Chinese Application No. 201010570238.X.

* cited by examiner

FOG-RESISTANT STRUCTURE AND PROTECTIVE DEVICE FOR EYES

CROSS REFERENCE TO RELATED APPLICATIONS

This application claims priority of Japanese application No. 2009-274968 filed on Dec. 2, 2009, the entire contents of which is hereby incorporated herein by reference.

BACKGROUND OF THE INVENTION

1. Field of the Invention

The present invention relates to a fog-resistant structure such as lenses for nearsighted glasses, farsighted glasses, and sunglasses; lenses for goggles for skiing and goggles for motorcycling; and shields for eye protection such as sports helmets and hard hats; and a protective device for eyes including the fog-resistant structure such as glasses, sunglasses, goggles, and helmet shield devices.

2. Description of the Related Art

Glass lenses and like fog in such a manner that heat generated from the face surface of the wearer causes a difference in temperature between the air contacting the lens inner surface facing the face surface and the external air contacting the lens outer surface, and water vapors in the air on the lens inner surface side condense on the lens inner surface.

In light of this, glass lenses are configured such that a transparent conductive film made of tin oxide, indium oxide, or the like is formed on the surface of the glass lenses, an electrode is fixed on upper and lower edges of the transparent conductive film, an electrode protection plate is fixed on the surface of each electrode, a power supply line is connected to each of the upper and lower electrodes, power is supplied from the power supply to the transparent conductive film for conduction, the lens temperature is increased to dry water vapors condensed on the lens inner surface, and thereby the glass lenses are prevented from fogging.

However, when such a glass lens configuration is applied to the goggle lenses for skiing and motorcycling or shields for sports helmets, the external temperature contacting the outer surface of the lenses or shields is extremely lowered by the high speeds during skiing and motorcycling to cause a significant difference in temperature between the face surface of the wearer and the lenses or shields. Therefore, a large power is needed to increase the temperature of the lenses or shields. Thus, there is a problem with wasted power consumption and large-sized power supply causing inconvenience of wearing.

In light of this, for example, Patent Literature 1 (Japanese Patent Laid-Open No. 50-147192) discloses a structure suitable for preventing fogging of goggle lenses for skiing and motorcycling or shields for sports helmets.

The structure disclosed in Patent Literature 1 is configured such that as illustrated in FIG. 9, a transparent conductive film 12 is formed on the entire surface of a lens 11, a linear electrode 13 and an electrode protection plate 14 are fixed to the upper and lower edges of the surface of the transparent conductive film 12 in this order, one end of a power supply line 15 is fixed to the upper and lower electrodes 13 or the upper and lower electrode protection plates 14, and the other end of the power supply line 15 is connected to a power switch. This structure is such that a spacer 16 made of an elastic, cold-resistant, and heat-resistant material and a separate lens 17 on the other surface of the spacer 16 are fixed to the transparent conductive film 12 side in this order, and a sealed empty space 18 is interposed between the transparent conductive film 12 and the separate lens 17.

However, even for the goggle lenses for skiing and motorcycling or shields for sports helmets, the temperature in a central region of a lens or shield is relatively lowered and the temperature in opposite side regions of the lens or shield is relatively increased, thus causing a difference in temperature in those regions.

The reason for causing such a difference in temperature is that each portion of the transparent conductive film having electrical resistance has different spacing between linear electrodes. More specifically, in opposite side portions of the lenses or shields, the spacing between linear electrodes is small and thus the electrical resistance is low; current is easy to flow and thus the amount of heat generation increases relatively, while in a central region of a lens or shield, the spacing between linear electrodes is large and thus the electrical resistance is high; current is difficult to flow and thus the amount of heat generation decreases relatively.

In order to secure the field of view of the helmet wearer, first, the temperature is increased to prevent fogging in the central portion of the lens or shield. However, when an electric current is applied to increase the temperature of the central region to a degree required to prevent fogging, an electric current higher than that thereof flows through the regions of opposite side portions, thereby causing wasted power consumption. In particular, a structure using a battery as the power supply such as helmet shields has a problem in that the available time of the anti-fog heater is very limited.

In order to solve such a problem, for example, Patent Literature 2 (Japanese Patent Laid-Open No. 2002-237371) discloses a helmet shield.

According to Patent Literature 2, as illustrated in FIG. 10, each of the linear electrodes 23 and 24 is divided into three split linear electrodes 23a to 23c and 24a to 24c respectively according to the difference in length in the conducting direction (vertical direction) in each portion of the transparent conductive film 22 heating the shield 21. These split linear electrodes are used for regulation such that an regulation is made on power supplied to the portions of the transparent conductive film 22 on opposite side regions 25 of the shield 21 and the portion of the transparent conductive film 22 on the central region 26 thereof so that each portion has substantially the same amount of heat generation or the central region 26 has a slightly larger amount of heat generation.

Unfortunately, the helmet shield disclosed in Patent Literature 2 has a problem in that in order to regulate power supplied to the transparent conductive film 22, a constant-voltage circuit having a plurality of output voltages needs to be interposed between the vertically divided linear electrodes 23a to 23c and 24a to 24c and the power supply or a power regulating controller needs to be provided, thereby complicating the structure and increasing the unit price of the product.

Further, the helmet shield disclosed in Patent Literature 2 has a problem in that in order to supply power to the transparent conductive film 22, power supply lines 27a to 27d need to be connected to the vertically divided linear electrodes 23a to 23c and 24a to 24c respectively, thereby complicating the wiring of the plurality of power supply lines 27a to 27d and causing an easy-to-fail and hard-to-maintain problem.

SUMMARY OF THE INVENTION

In view of this, the present invention has been made to solve the above conventional problems, and an object of the present invention is to provide a fog-resistant structure and a protective device for eyes in which each region of a lens or shield has no difference in temperature without regulating power supplied to a transparent conductive film, thereby eliminating wasted power consumption and allowing even a structure using a battery as a power supply to have much longer available time.

Further, another object of the present invention is to provide a fog-resistant structure and a protective device for eyes which have a simplified structure in which power supply lines are connected to linear electrodes to supply power to the transparent conductive film and which are difficult to fail and easy to maintain.

Therefore, the fog-resistant structure of the present invention is configured such that a transparent conductive film is formed on one surface of a lens or shield, a linear electrode is provided on upper and lower portions of the surface of the lens or shield so that each of the central region and the opposite side regions of the lens or shield has substantially equal spacing between the upper and lower linear electrodes.

Further, the fog-resistant structure of the present invention includes an insulating portion on opposite side ends of the lens or shield, in which each of opposite ends of the linear electrodes is connected to the power supply line.

Further, the fog-resistant structure of the present invention is configured such that each of opposite ends of the linear electrodes is used as a first connection terminal and each of opposite ends of the power supply line is used as a second connection terminal; in opposite end portions of the lens or shield, one end of each of the linear electrodes is disposed close to each other; and the first connection terminal of each of opposite ends of the linear electrodes are pressure-bonded to the second connection terminal of each of opposite ends of the power supply line.

Further, the fog-resistant structure of the present invention is such that the insulating portion is a non-formed portion of the transparent conductive film.

Further, the fog-resistant structure of the present invention is such that a separate lens or shield is attached on a side on which the transparent conductive film of the lens or shield is formed and a sealed empty space is interposed between the transparent conductive film and the separate lens or shield.

The protective device for eyes of the present invention includes the fog-resistant structure.

The present invention is configured as described above and thus each region of the lens or shield has no difference in temperature without regulating power supplied to the transparent conductive film, thereby eliminating wasted power consumption and allowing even a structure using a battery as the power supply to have much longer available time.

Further, the present invention has a simplified structure in which the power supply lines are connected to the linear electrodes and is difficult to fail and easy to maintain.

DESCRIPTION OF THE PREFERRED EMBODIMENTS

Figure 1:
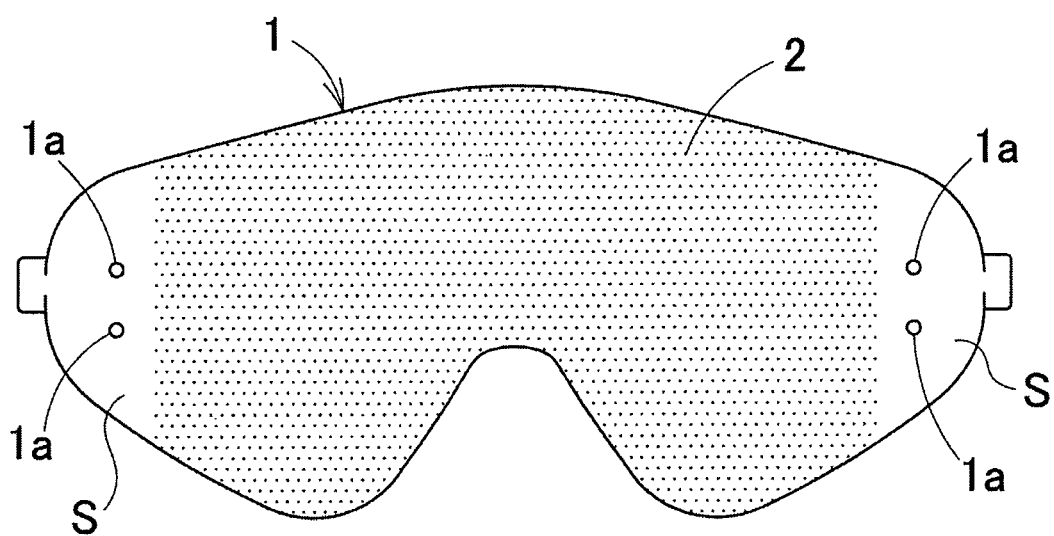
FIG. 1 is an explanatory drawing illustrating an example of a state in which a transparent conductive film is formed on one surface of the lens or shield according to the fog-resistant structure of the present invention.

Hereinafter, embodiments for carrying out the fog-resistant structure of the present invention will be described in detail based on the drawings.

FIGS. 1 to 5 illustrate a lens 1 of a goggle for skiing serving as the fog-resistant structure of the present invention. A transparent conductive film 2 is formed on one surface of the lens 1 whose opposite side ends include an insulating portion S. The transparent conductive film 2 is formed by a sputtering method or the like. At this time, the insulating portion S is formed by masking the opposite side ends. Note that anti-fog coating (unillustrated) is performed on the other surface of the lens 1 as needed.

Then, each linear electrode 3 is disposed on upper and lower portions of the surface on which the transparent conductive film 2 of the lens 1 is formed. Each of the opposite ends of the linear electrodes 3 is connected to a power supply line 4 at the insulating portion S.

Further, according to the present invention, the linear electrode 3 is made of a conductive paste. The conductive paste is applied in such a manner that each of the central portion and the opposite side portions of the lens 1 has substantially equal spacing between the upper and lower linear electrodes 3 on the surface of the transparent conductive film 2.

Further, the present invention can be configured such that a separate lens 5 is attached on a side on which the transparent conductive film 2 of the lens 1 is formed to form a double lens and a sealed empty space is interposed between the transparent conductive film 2 and the separate lens 5.

A transparent resin with 80° C. or higher deflection temperature under flexural load (ASTM-D648 method) of polycarbonate and like is used as the base material of the lens 1. Note that when a shield (unillustrated) is used instead of the lens 1, a similar base material is used.

ITO (indium oxide/tin oxide), ZnO (zinc oxide), IZO (indium oxide/zinc oxide), AZO (zinc oxide/aluminum oxide), GZO (zinc oxide/gallium oxide), Au (gold), or like is used as the transparent conductive film 2. Coating can be performed not only by the sputtering but also by vapor deposition and printing application. In particular, the use of ITO for sputtering coating is desirable from the point of view of the surface resistance, transmittance and like. When ITO is used, the surface resistance can be equal to or less than 50 $\Omega/cm^2$, the film thickness can be equal to or greater than 100 nm, and the visible light transmittance can be equal to or greater than 60%.

Figure 2:
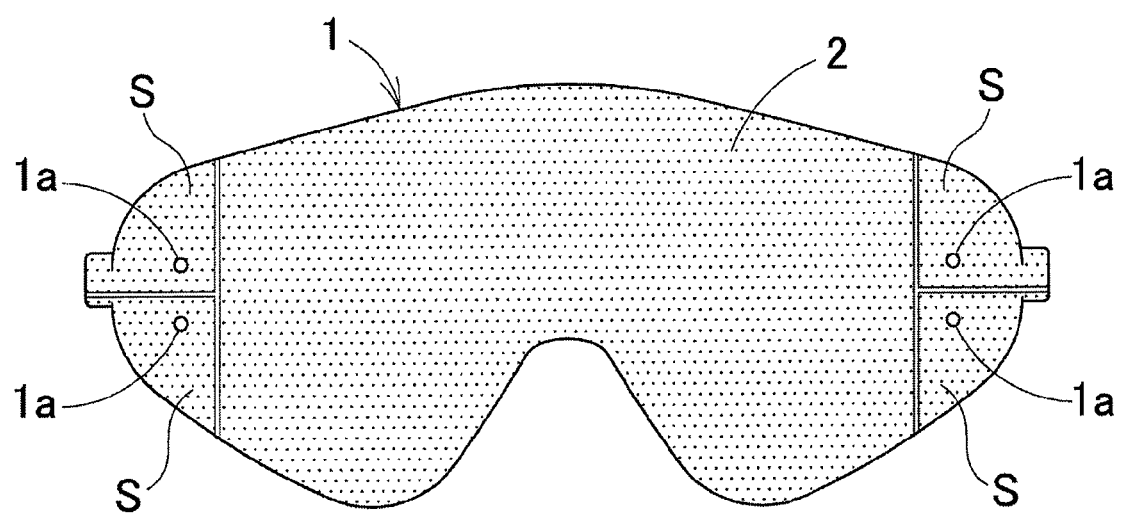
FIG. 2 is an explanatory drawing illustrating another example of a state in which a transparent conductive film is formed on one surface of the lens or shield according to the fog-resistant structure of the present invention.

As illustrated in FIG. 1, it is preferable that the insulating portion S is formed such that the transparent conductive film 2 is not formed on opposite side ends of one surface of the lens 1, because it is easy to form the insulating portion S and it is easy to connect the linear electrode 3 and the power supply line 4. Alternatively, as illustrated in FIG. 2, the transparent conductive film 2 may be divided into at least left, right, up, and down portions through the non-formed portion. Note that when the insulating portion S is formed by dividing the transparent conductive film 2 into the left, right, up, and down portions, the power supply line 4 is connected to the linear electrode 3 described later in such a manner that opposite ends of the linear electrode 3 disposed on an upper portion of the lens 1 are connected in the upper portions of the transparent conductive film 2 divided left and right portions and opposite ends of the linear electrode 3 disposed on a lower portion of the lens 1 are connected in the lower portions of the transparent conductive film 2 divided left and right portions.

Figure 3:
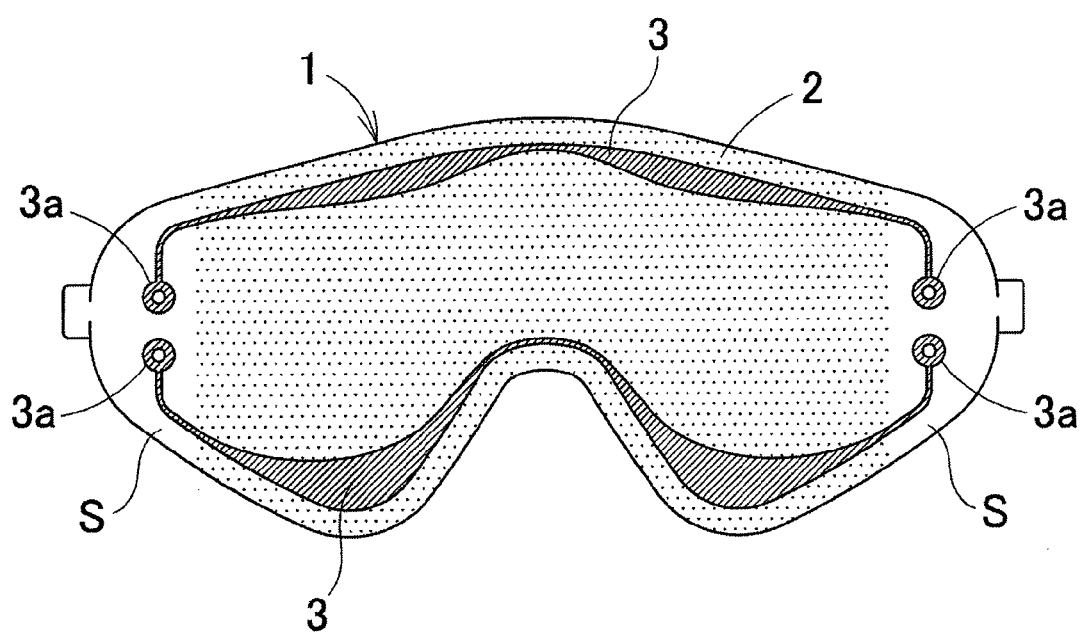
FIG. 3 is an explanatory drawing illustrating an example of a state in which linear electrodes are disposed on the film-formed surface of the lens or shield on which the transparent conductive film is formed according to the fog-resistant structure of the present invention.
Figure 4:
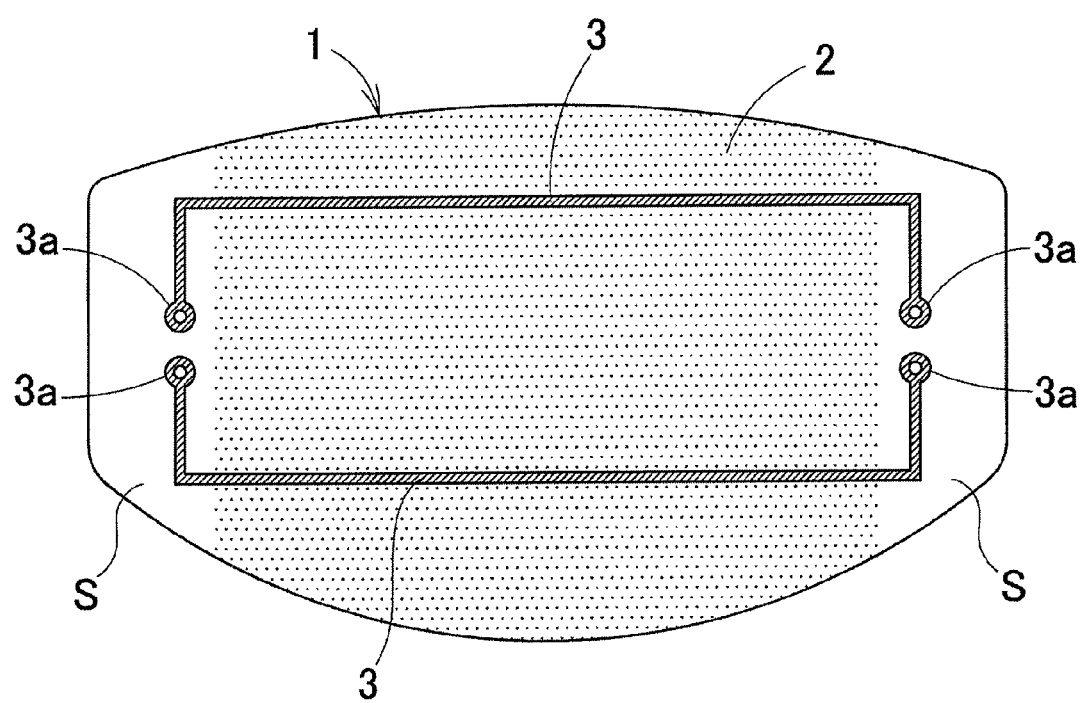
FIG. 4 is an explanatory drawing illustrating another example of a state in which linear electrodes are disposed on the film-formed surface of the lens or shield on which the transparent conductive film is formed according to the fog-resistant structure of the present invention.

The linear electrode 3 is made of a conductive paste containing gold, silver, copper, nickel, carbon, or the like, but a silver paste is desirable in terms of low-temperature curing. The conductive paste is disposed by silk print so as to provide substantially equal spacing between the upper and lower linear electrodes 3 on the surface of the transparent conductive film 2 throughout a full uninterrupted lateral extent of the transparent conductive film. In order to dispose the conductive paste so as to provide substantially equal spacing between the upper and lower linear electrodes 3, as illustrated in FIG. 3, the visual field width may be adjusted by changing the line width from 1 to 20 mm or as illustrated in FIG. 4, the visual field width may be adjusted by fixing the line width to 1 to 3 mm. Note that when the line width is less than 1 mm, the resistance increases unfavorably to generate heat.

Further, each of opposite ends of the linear electrodes 3 is formed as a first connection terminal 3a such as a ring terminal, each first connection terminal 3a is located close to each other in the insulating portion S on opposite side ends of the lens 1, and the closely located first connection terminal 3a is connected to the respective power supply line 4.

Figure 5:
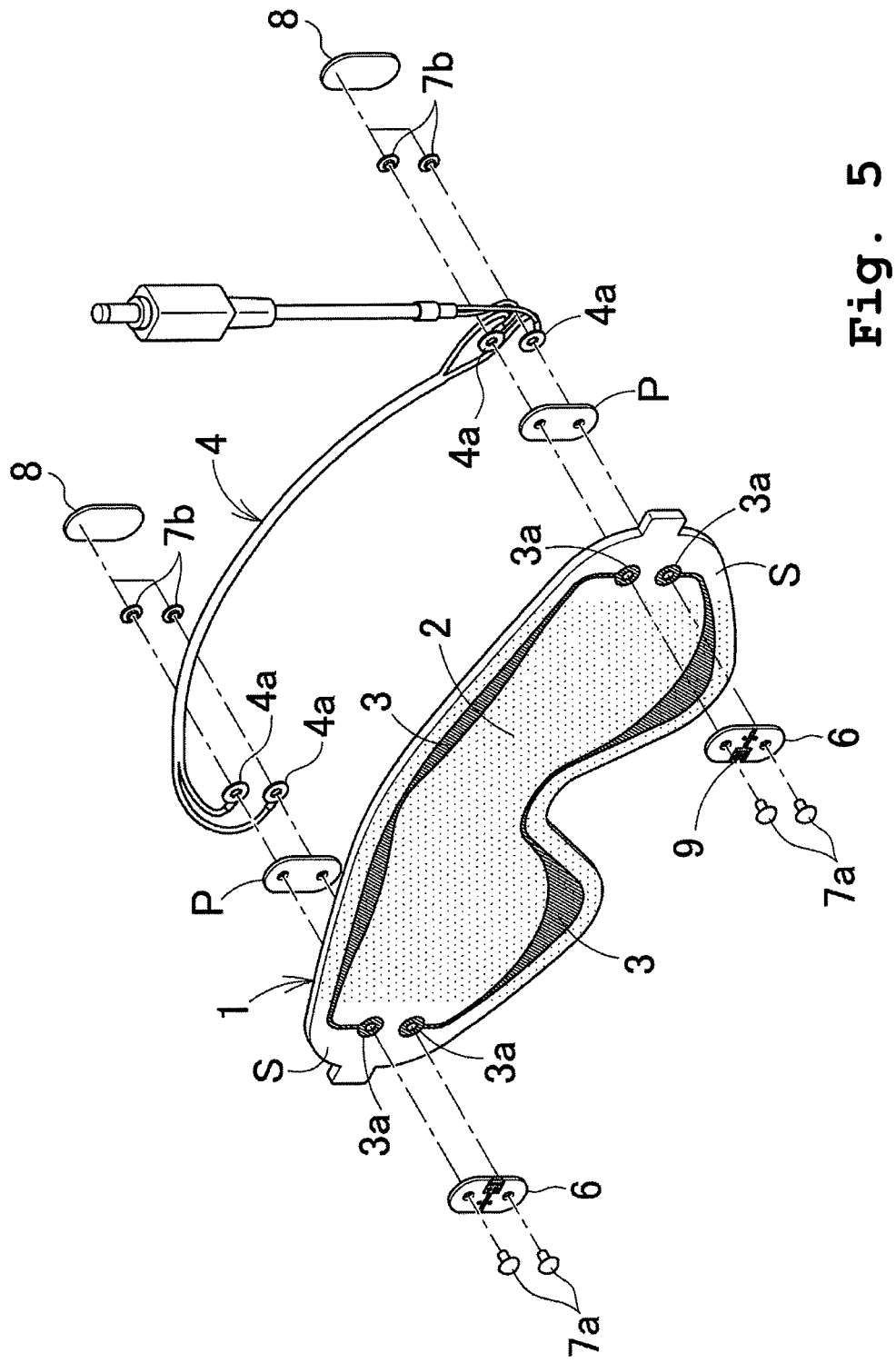
FIG. 5 is an exploded perspective view of the fog-resistant structure of the present invention.

As illustrated in FIG. 5, each of the opposite ends of the power supply line 4 is formed as a second connection terminal 4a such as a ring terminal, a metal crimp 7a is passed through a base plate 6, whose both surfaces are masked with metal, the metal crimp 7a is inserted into a crimp hole 1a formed in the lens 1, a first connection terminal 3a of each of the opposite ends of the linear electrode 3 is crimp-bonded to a second connection terminal 4a of each of the opposite ends of the power supply line 4 with the metal crimp 7a and the acceptor 7b, and the crimp-bonded portion is covered with a protective seal 8. At this time, a packing P made of silicon, closed-cell foam sponge, or the like is interposed between the first and second connection terminals 3a and 4a, and then the double lens can be airtight. Further, an LED 9 is attached to the base plate 6. When power is supplied from the power supply line 4 to the linear electrode 3, the LED 9 emits light. Thus, it is easy to confirm the presence or absence of conduction.

Figure 6:
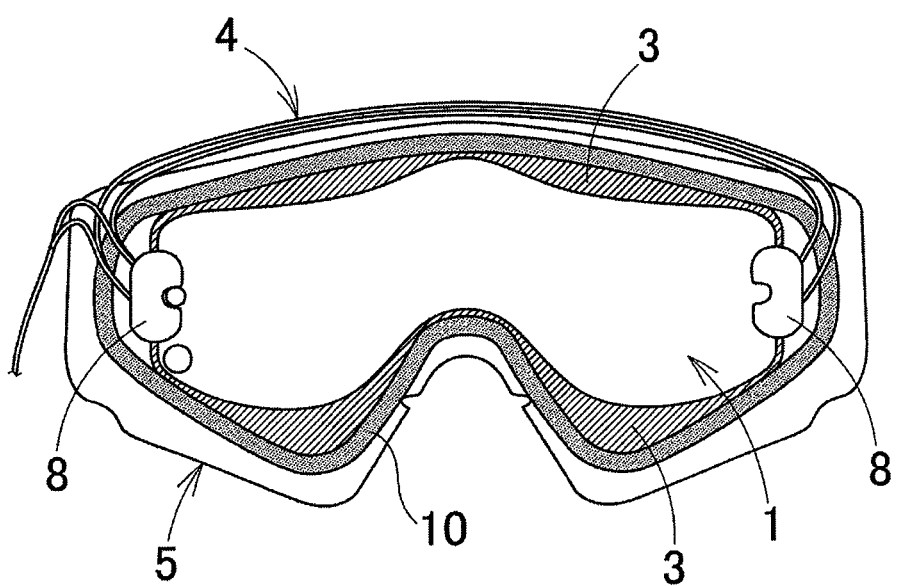
FIG. 6 is a rear view of a double lens to which the fog-resistant structure of the present invention is applied.

Further, a double lens is formed airtight in such a manner that as illustrated in FIG. 6, on a side on which the transparent conductive film 2 of the lens 1 is formed, a separate lens 5 slightly larger than the lens 1 is pressure-bonded and attached thereto with an adhesive resin 10 with a thickness of 1 to 10 mm sandwiched therebetween. The separate lens 5 to be attached may include the transparent conductive film 2 formed thereon and the linear electrode 3 disposed thereon like the lens 1, as well as a function such as modulated light, polarized light, hard coating, water repellency, reflective film, and anti-reflection film.

Note that the illustrated examples focus on the lens 1 for goggles for skiing, but apparently the present invention may be applied to shields for sports helmets as well.

Figure 7:
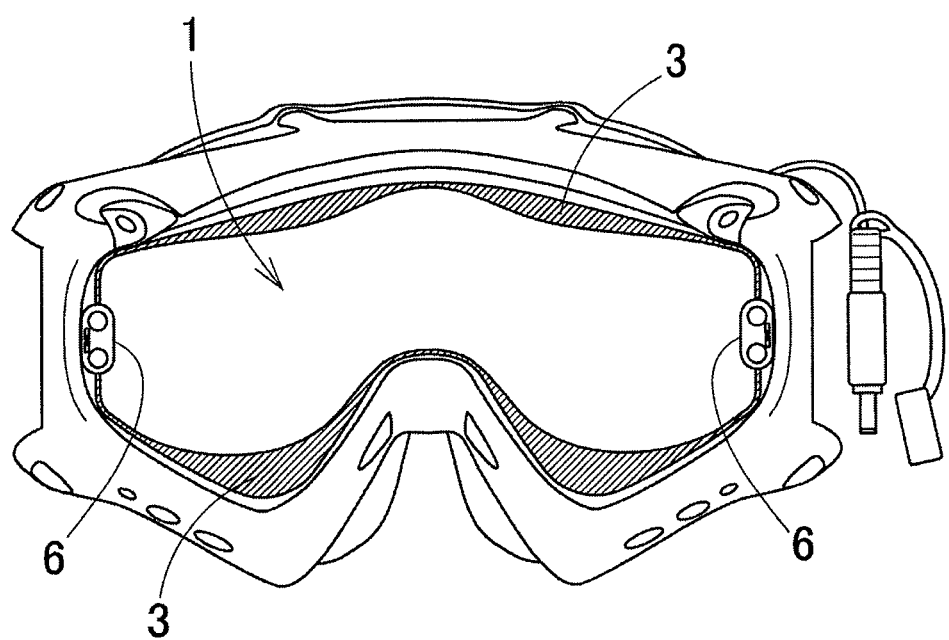
FIG. 7 is a front view of a goggle body of a goggle for skiing illustrated as a protective device for eyes of the present invention.

FIG. 7 illustrates a protective device for eyes including the lens for use in goggles for skiing, but the protective device for eyes of the present invention may be applied to the other type of sports goggles, goggles for motorcycling, lenses for near-sighted glasses, farsighted glasses, and sunglasses, and shield devices such as sports helmets and hard hats.

Example 1

A polycarbonate resin sheet (a thickness of 1 mm) whose surface was covered with anti-fog coating was punched out into a goggle-like lens shape. Masking was made on the reverse side of the lens covered with anti-fog coating, so as to extend within 20 mm from each of the opposite ends of the lens. Then, ITO sputtering was performed to form an ITO transparent conductive film with a film thickness of 190 nm and a surface resistance of 30 $\Omega/cm^2$.

Then, a linear conductive paste made of silver paste was disposed on the ITO transparent conductive film by silk printing. One of the two line shapes was a shape of a line along the inner circumference of the upper half of the outer circumference of the goggle lens with a line width varying from 1 to 5 mm; and the other one was a shape of a line along the inner circumference of the lower half thereof with a line width varying from 1 to 15 mm. The transparent conductive film portion interposed between the two lines formed a transparent heater.

Each of the opposite ends of the upper and lower two conductive pastes was formed into a shape with an external diameter of 3 mm and a ring terminal shape whose central portion had a 2.5 mm hole. An LED mounting base plate with a thickness of 0.5 mm which was metaled on both surfaces and had an LED and a resistor mounted on an upper portion of the one surface was disposed on one immediately above the surface so as to contact a surface in which no LED was mounted immediately above the conductive paste surface; and likewise, a base plate with a thickness of 0.5 mm of which both surfaces were masked by metal was disposed on the other immediately above the surface as well.

Further, each chloroprene closed-cell foam sheet with a thickness of 1 mm having adhesive on one side was disposed on an anti-fog coating surface side of the opposite ends of the conductive paste, a total of four ring terminals for the power supply lines each serving as a positive or negative terminal were disposed on the opposite upper and lower ends, the four places were pressure-bonded with a metal crimp (a length of 5 mm, a head diameter of 5 mm, and a bar diameter of 2.5 mm) to form a heater inner lens having an electrode for receiving power supply; and a resin sheet made of a closed-cell foam body with a thickness of 2 mm and a width of 5 mm having adhesive on both sides was pressure-bonded along the outer circumference portion of the lens, and a polycarbonate resin base plate (with a thickness of 0.8 mm) hard coated on one side was attached to each other with the hard coated surface outside to form a double lens.

When a current of 500 mA at 5 V was supplied from the power supply line to the conductive paste on the above configured double lens, the LED emitted light and the temperature of the inner lens surface (anti-fog coating surface) was 35° C. in the 20° C. environment. When water vapor with 20° C. and 100% RH was sprayed, no fogging occurred during conduction.

When water vapor with 20° C. and 100% RH was sprayed in a state without conduction, no fogging occurred in the beginning, but fogging occurred in ten minutes. When power was supplied again at the time when half of the lens surface fogged, the fog disappeared in ten minutes.

Five minutes later, power was turned off and water vapor with 20° C. and 100% RH was sprayed. Then, no fogging occurred in the beginning, but fogging occurred in ten minutes. When power was supplied again at the time when half of the lens surface fogged, the fog disappeared in ten minutes.

Further, water was applied to the lens surface in the minus 20° C. environment. When the water was frozen and then power was supplied, the frozen water was turned to liquid water in five minutes.

Note that even if the double lens was dipped in 50° C. water for 120 hours, no water entered inside the double lens.

Then, the double lens of example 1 was tested assuming that the expected regions are a ski resort area and a cold region as well as an unexpected extremely cold region; and the respective test temperatures are 25° C., 0° C., and −15° C. using a fully charged lithium-ion battery KBC-L3 (SANYO Electric Co., Ltd., output: DC 5.0 V/500 mA) as the power supply. When the measurements were made on the operating times and the changes in internal temperature in the central portion and the opposite side portions of the inner lens of the double lens, the measurement results as illustrated in Table 1 and FIG. 8 were obtained.

TABLE 1

| Expected regions | Test temperatures | During no conduction | During conduction | Measured current values | Operating times |
|---|---|---|---|---|---|
| Ski resort area | 25° C. | 26° C. | 35° C. | 0.31 A:14.8 Ω | 4:30 |
| Cold region | 0° C. | 8° C. | 15° C. | 0.33 A:14.1 Ω | 4:00 |
| Extremely cold region | −15° C. | −9° C. | −1° C. | 0.34 A:13.7 Ω | 2:30 |

Figure 8:
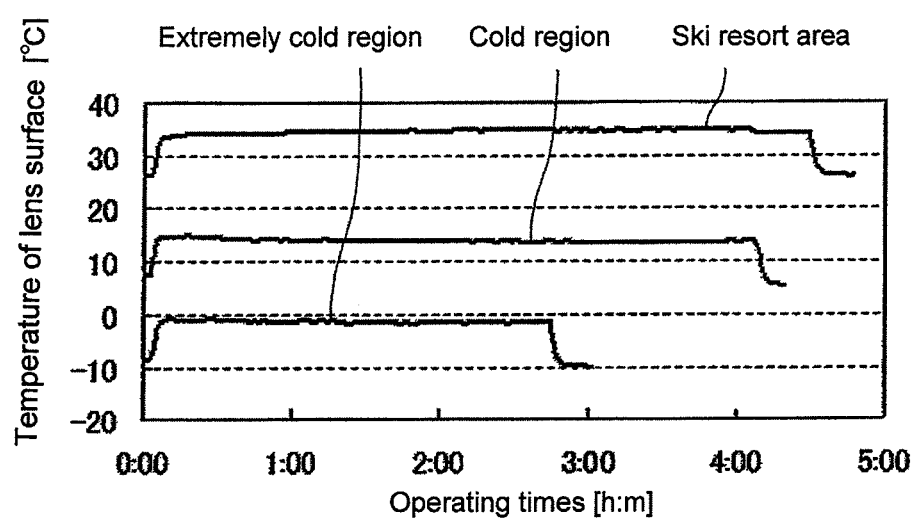
FIG. 8 is a graph illustrating an operating time of the fog-resistant structure of the present invention and a change in inner temperature of an inner lens of the double lens.
Figure 9:
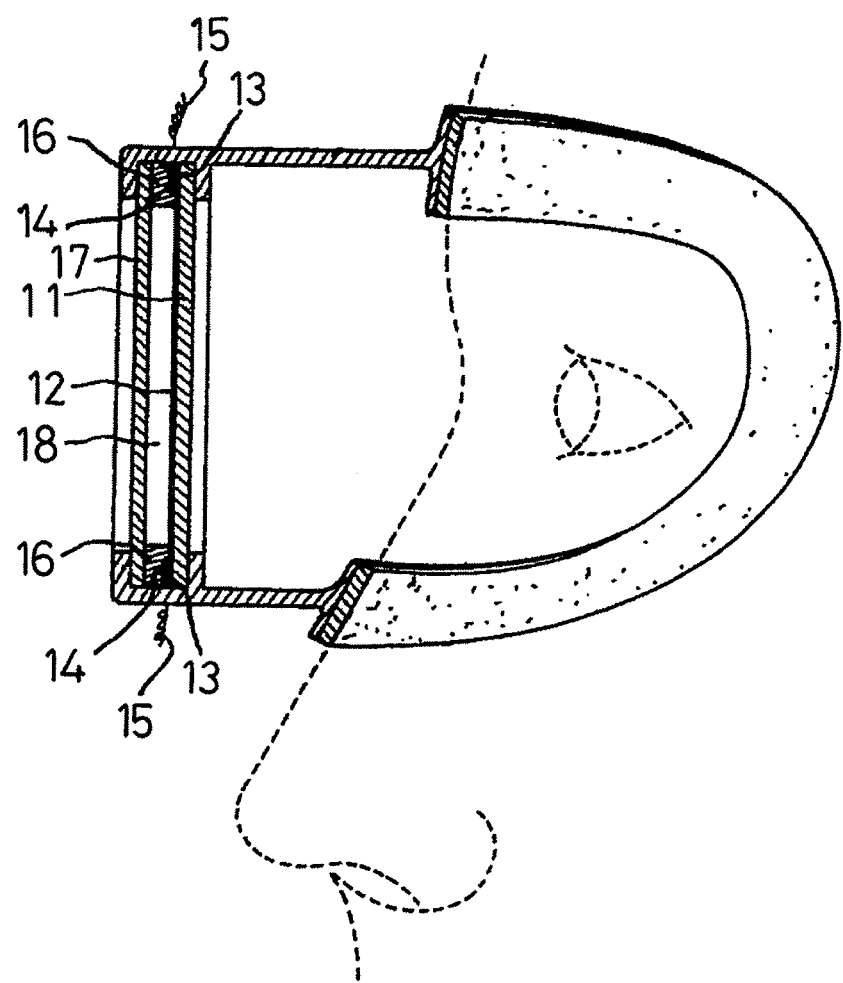
FIG. 9 is a sectional view of essential parts of a goggle body of a goggle for skiing illustrated to which conventional fog-resistant structure is applied.
Figure 10:
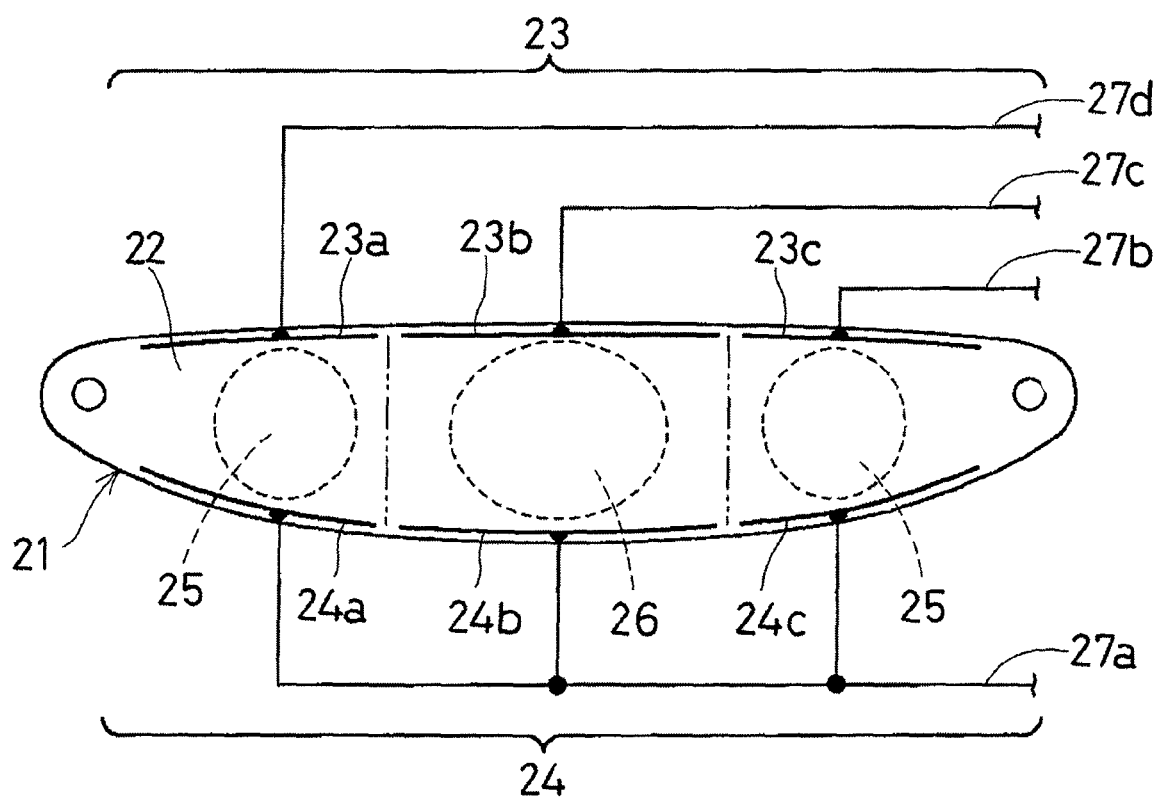
FIG. 10 is an explanatory drawing illustrating an external appearance of a shield of a helmet for motorcycling to which conventional fog-resistant structure is applied.

As illustrated in Table 1 and FIG. 8, in the ski resort area and the cold region as well as the unexpected extremely cold region, the operating times were 2 hours and 30 minutes to 4 hours and 30 minutes, and the internal temperature in the central portion and the opposite side portions of the inner lens of the double lens were constant during conduction and increased 7 to 9° C. compared to during no conduction. Thus, the double lens had much longer available time and excellent anti-fog effects as well.

What is claimed is:

1. A wearable fog-resistant structure, comprising:
   a lens or shield having a surface with opposite side ends, and with upper and lower portions extending along upper and lower peripheral edges, respectively;
   a transparent conductive film formed on the surface of the lens or shield;
   an upper linear electrode provided on the upper portion of the surface adjacent the upper peripheral edge, a lower linear electrode provided on the lower portion of the surface adjacent the lower peripheral edge;
   each electrode having opposite ends on the opposite side ends of the surface, an outer border extending between said opposite ends and contoured to follow an adjacent peripheral edge of the lens or shield, and an inner border extending between said opposite ends and spaced from the outer border by a width;
   wherein the width of at least one electrode of the upper linear electrode and the lower linear electrode varies to maintain substantially equal spacing between the inner border of the upper linear electrode and the inner border of the lower linear electrode throughout a full uninterrupted lateral extent of the transparent conductive film;
   wherein the lens or shield has a central vertical region and opposite side regions on opposite sides of the central vertical region, the central vertical region being narrower in height than the opposite side regions, and the width of the at least one electrode being larger in the opposite side regions than in the central vertical region, wherein variation of the width of said at least one electrode results in no difference in temperature between the central vertical region and the opposite side regions of the lens or shield when electrical power is supplied to the transparent conductive film;
   further comprising power supply lines, and wherein the surface includes an insulating portion on the opposite side ends of the surface of the lens or shield, in which each of the opposite ends of the upper linear electrode and the lower linear electrode are connected to a respective end of the power supply lines;
   wherein each of the opposite ends of the upper linear electrode and the lower linear electrode are used as a first connection terminal and each of opposite ends of the power supply lines are used as a second connection terminal; in opposite end portions of the lens or shield, one end of each of the upper linear electrode and the lower linear electrode are disposed close to each other; and the first connection terminal of each of the opposite ends of the upper linear electrode and the lower linear electrode are pressure-bonded to the second connection terminal of each of the opposite ends of the power supply lines; and
   wherein the first connection terminal of each of the opposite ends of the upper linear electrode and of the lower linear electrode are pressure-bonded by crimp bonding to the second connection terminal of each of the opposite ends of the power supply lines.

2. The wearable fog-resistant structure according to claim 1, wherein the width of both the upper linear electrode and the lower linear electrode varies to maintain said substantially equal spacing.

3. A protective device for eyes including the wearable fog-resistant structure according to claim 2.

4. The wearable fog-resistant structure according to claim 1, wherein the width of the at least one electrode varies from 1 to 20 mm.

5. The wearable fog-resistant structure according to claim 4, wherein width of the upper linear electrode varies from 1 to 5 mm, and width of the lower linear electrode varies from 1 to 15 mm.

6. The wearable fog-resistant structure according to claim 1, wherein each first terminal connector and each second terminal connector comprises a ring terminal.

7. The wearable fog-resistant structure according to claim 1, wherein said crimp bonding includes a base plate mounting an LED which emits light when power is supplied from the power supply lines to at least one of the upper linear electrode and the lower linear electrode.

8. The fog-resistant structure according to claim 1, wherein the insulating portion is a non-formed portion of the transparent conductive film.

9. The fog-resistant structure according to claim 8, wherein a separate lens or shield is attached on a side on which the transparent conductive film of the lens or shield is formed and a sealed empty space is interposed between the transparent conductive film and the separate lens or shield.

10. A protective device for eyes including the fog-resistant structure according to claim 8.

11. A protective device for eyes including the fog-resistant structure according to claim 9.

12. The fog-resistant structure according to claim 1, wherein the insulating portion is a non-formed portion of the transparent conductive film.

13. The fog-resistant structure according to claim 12, wherein a separate lens or shield is attached on a side on which the transparent conductive film of the lens or shield is formed and a sealed empty space is interposed between the transparent conductive film and the separate lens or shield.

14. A protective device for eyes including the fog-resistant structure according to claim 12.

15. A protective device for eyes including the fog-resistant structure according to claim 13.

16. The fog-resistant structure according to claim 1, wherein a separate lens or shield is attached on a side on which the transparent conductive film of the lens or shield is formed and a sealed empty space is interposed between the transparent conductive film and the separate lens or shield.

17. A protective device for eyes including the fog-resistant structure according to claim 16.

18. The fog-resistant structure according to claim 1, wherein a separate lens or shield is attached on a side on which the transparent conductive film of the lens or shield is formed and a sealed empty space is interposed between the transparent conductive film and the separate lens or shield.

19. A protective device for eyes including the fog-resistant structure according to claim 18.

20. A protective device for eyes including the fog-resistant structure according to claim 1.

21. A protective device for eyes including the fog-resistant structure according to claim 1.

* * * * *